(12) United States Patent
Weinberg et al.

(10) Patent No.: US 11,554,269 B2
(45) Date of Patent: Jan. 17, 2023

(54) METHOD, SYSTEM AND COMPONENTS FOR SELECTIVE MAGNETIC PARTICLE MOTION

(71) Applicant: Weinberg Medical Physics, Inc., North Bethesda, MD (US)

(72) Inventors: Irving Weinberg, North Bethesda, MD (US); Bradley English, North Bethesda, MD (US)

(73) Assignee: WEINBERG MEDICAL PHYSICS, INC., North Bethesda, MD (US)

( * ) Notice: Subject to any disclaimer, the term of this patent is extended or adjusted under 35 U.S.C. 154(b) by 358 days.

(21) Appl. No.: 16/778,620

(22) Filed: Jan. 31, 2020

(65) Prior Publication Data

US 2020/0246629 A1    Aug. 6, 2020

Related U.S. Application Data

(60) Provisional application No. 62/800,132, filed on Feb. 1, 2019.

(51) Int. Cl.
*A61N 2/02* (2006.01)
*H01F 7/02* (2006.01)
*G01R 33/383* (2006.01)

(52) U.S. Cl.
CPC ............ *A61N 2/02* (2013.01); *G01R 33/383* (2013.01); *H01F 7/0278* (2013.01)

(58) Field of Classification Search
CPC ................... A61N 2/00; A61N 2/12
See application file for complete search history.

(56) References Cited

U.S. PATENT DOCUMENTS

| | | | | |
|---|---|---|---|---|
| 8,836,329 B2 * | 9/2014 | Weinberg | ............. | G01R 33/445 |
| | | | | 324/307 |
| 8,971,988 B2 * | 3/2015 | Borgert | ................ | A61B 5/6814 |
| | | | | 600/409 |
| 9,380,959 B2 | 7/2016 | Weinberg et al. | | |
| 10,300,011 B1 * | 5/2019 | Khizroev | ................ | A61N 2/004 |
| 2012/0058441 A1 * | 3/2012 | Boeve | ................ | G01R 33/1276 |
| | | | | 432/36 |
| 2012/0065491 A1 * | 3/2012 | Borgert | ................ | A61B 5/0042 |
| | | | | 600/409 |
| 2016/0096030 A1 * | 4/2016 | Nacev | .................... | A61B 5/055 |
| | | | | 600/12 |

* cited by examiner

*Primary Examiner* — Ramon M Barrera
(74) *Attorney, Agent, or Firm* — Barnes & Thornburg LLP

(57) ABSTRACT

A method, apparatus and components thereof enable selective or differentiated manipulation of at least one of a plurality of particles located in a region of space via magnetic field generation and variation.

12 Claims, 5 Drawing Sheets

METHOD, SYSTEM AND COMPONENTS FOR SELECTIVE MAGNETIC PARTICLE MOTION

CROSS REFERENCE AND PRIORITY CLAIM

This patent application claims priority to U.S. Provisional Patent Application No. 62/800,132, entitled "SELECTIVE MAGNETIC PARTICLE MOTION," filed Feb. 1, 2019, the disclosure of which being incorporated herein by reference in its entirety.

FIELD OF USE

Disclosed embodiments enable selective or differentiated manipulation of at least one of a plurality of particles located in a region of space via magnetic field generation and variation.

BACKGROUND

It is known how to apply magnetic fields in a region of a magnetizable particle in particular sequences so as to push or pull the magnetic particle. See U.S. Pat. No. 9,380,959 issued to Weinberg and entitled "MRI-GUIDED NANOPARTICLE CANCER THERAPY APPARATUS AND TECHNOLOGY" (incorporated by reference in its entirety; hereafter the "'959 Patent").

SUMMARY

Disclosed embodiments provide an application of prior work regarding the memory property of some magnetizable particles, in which particles magnetized by an initially-applied magnetic field external to the particle can retain their magnetization after the external magnetic field was removed.

Disclosed embodiments are based on the recognition that, if a new magnetic gradient pulse of short duration is applied in an appropriate direction (as specified in the '959 Patent), the particle can be repelled by this new gradient pulse to provide technical utility for manipulation of magnetic particles for the purposes of a medical practitioner to perform treatment or therapy to a living body.

Disclosed embodiments enable the ability to produce and vary magnetic fields in a region of space to selectively manipulate a plurality of particles whereby at least one part of at least one particle retains its magnetic polarization after reduction or removal of magnetic field from the at least one part of the at least one particle.

BRIEF DESCRIPTION OF THE FIGURES

The detailed description particularly refers to the accompanying figures in which.

DETAILED DESCRIPTION

Prior work by the inventors took advantage of the memory property of some magnetizable particles, in which particles magnetized by an initially-applied magnetic field external to the particle could retain their magnetization after the external magnetic field was removed. A useful property of this retention results in that, if a new magnetic gradient pulse of short duration is applied in an appropriate direction (as specified in the '959 Patent), the particle can be repelled by this new gradient pulse provided that the pulse duration is limited to be too short to permit the particle to fully rotate around to accommodate, e.g., align with, the force of the new gradient pulse.

Disclosed embodiments provide and application of this principle to provide technical utility for manipulation of magnetic particles for the purposes of a medical practitioner to perform treatment or therapy to a living body.

For example, for the purposes of a medical practitioner delivering therapy to a patient using more than one magnetic particle, it would be helpful to the practitioner to be able to manipulate a magnetic particle that was in one location without affecting a magnetic particle in another location. For example, a practitioner might want to place magnetic particles in a spatial distribution within a living body of a patient or subject that conformed to the size and shape of one tumor location and then move a second set of particles into a spatial distribution corresponding to a second tumor location within the living body. Disclosed embodiments are directed at providing an method, apparatus and components thereof for accomplishing this and related tasks.

The '959 Patent taught that electropermanent magnets can be used to build systems for Magnetic Resonance Imaging (MRI) and magnetic particle manipulation and therapy. In such systems, each electropermanent magnet typically consists of a cylindrical core of magnetizable material (e.g. AlNiCo, ferrite) within a conductive coil, through which a current is pulsed. The current pulse though the coil creates a magnetic field that magnetizes the core. That core remains magnetized even after the current pulse is completed and the magnetic field external to the particle is reduced. The core may be composed of multiple magnetizable materials, rather than a single solid core. This multiplicity may be useful to reduce skin effects that might otherwise reduce the magnetization of the core for a given applied current.

This core magnetization property is useful because it allows the electropermanent magnet to generate a magnetic field without the need for continued current flow, thereby reducing overall energy requirements.

Figure 1:
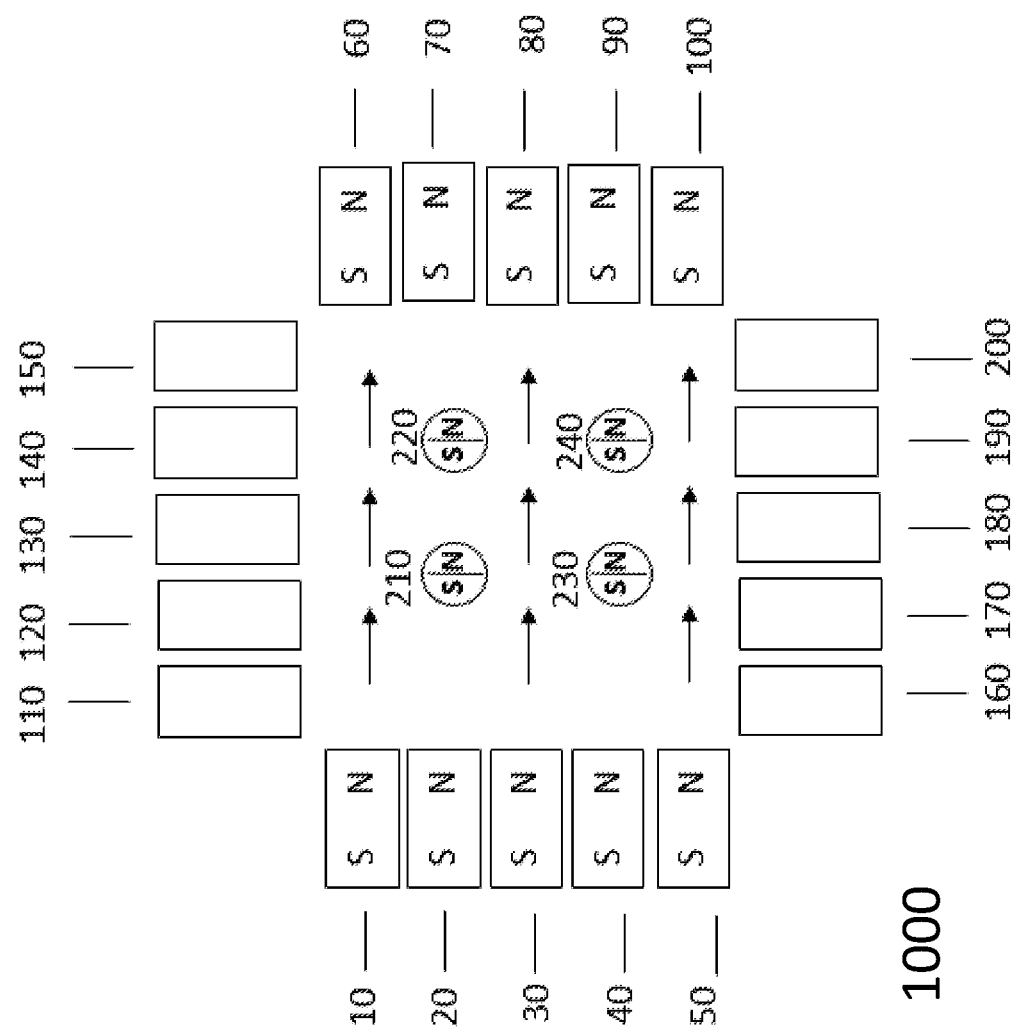
FIG. 1 illustrates an example of an initial configuration process for an apparatus in a Magnetizing State in accordance with the disclosed embodiments.

FIG. 1 illustrates an example of an initial configuration process for an apparatus 1000 configured in accordance with the disclosed embodiments. As shown in FIG. 1, the apparatus 1000 includes multiple devices 10-200 each configured to be capable of generating magnetic fields. The apparatus 1000 also includes multiple magnetizable particles at locations 210-240 within a region of interest affected by these magnetic fields. For the purpose of this specification, the term "region of interest" means a region of space where the magnetizable particles are intended by the operator to be located in, moved into, moved from, or activated in some way (for example, though heating from applied alternating magnetic fields). It should be understood that the apparatus 1000 also includes various control and power supply elements not illustrated specifically in FIG. 1 but understood to be present based on the teachings of the '959 Patent.

In an initial configuration illustrated in FIG. 1, the devices 10-100 may be implemented as electropermanent magnets. Those electropermanent magnets 10-100 are activated through the application of electrical currents so as to have initial magnetic orientations indicated in the figure by "N-S" pole markings on each electropermanent magnet 10-100. As shown in FIG. 1, the electropermanent magnets 110-200 have not yet been magnetized by application of electrical currents.

As shown in FIG. 1, a uniform magnetic field is indicated by small arrows in the region of interest between the electropermanent magnets 10-100. For the purpose of this specification, the term "uniform" means the magnetic field acts on each particle similarly within the region of interest.

In practical implementation, a typical uniformity specification would mean the magnetic field within the region of space is within 10% of the average magnetic field in that region of space.

Four magnetizable particles at locations 210-240 are shown in the region of interest between the electropermanent magnets 10-200. In operation, the particles at locations 210-240 are magnetized by the initial magnetic field set up by the electropermanent magnets 10-100. The magnetization vector of each particle is indicated by the "S-N" label shown within the particles at locations 210-240. It should be understood that the orientation may be in a different direction than as shown in the illustration. It should be understood that fewer or more particles may be in the region of interest, and that the use of four particles is for illustration. It should be understood that the particles at specific locations (for example the particle at location 210) may be slightly moved from that location but is still understood to be the particle which was effectively at location 210.

For the purpose of clarity in this specification, the initial configuration of electropermanent magnets and particles shown in FIG. 1 is termed the "Magnetizing State."

Note, although the illustration of electropermanent magnets in FIG. 1 is rectangular (both in their shape and in their relative configuration to one another) and shown in two dimensions, it should be understood that the electropermanent magnets may be shaped in various configurations and that sets of electropermanent magnets can be arranged in some other configuration (for example, circular or oval) and that this arrangement can be extended in the third dimension, either uniformly (for example, to create a cubic system) or in some other arrangement (for example, to create an ovoid-shaped system).

Figure 2:
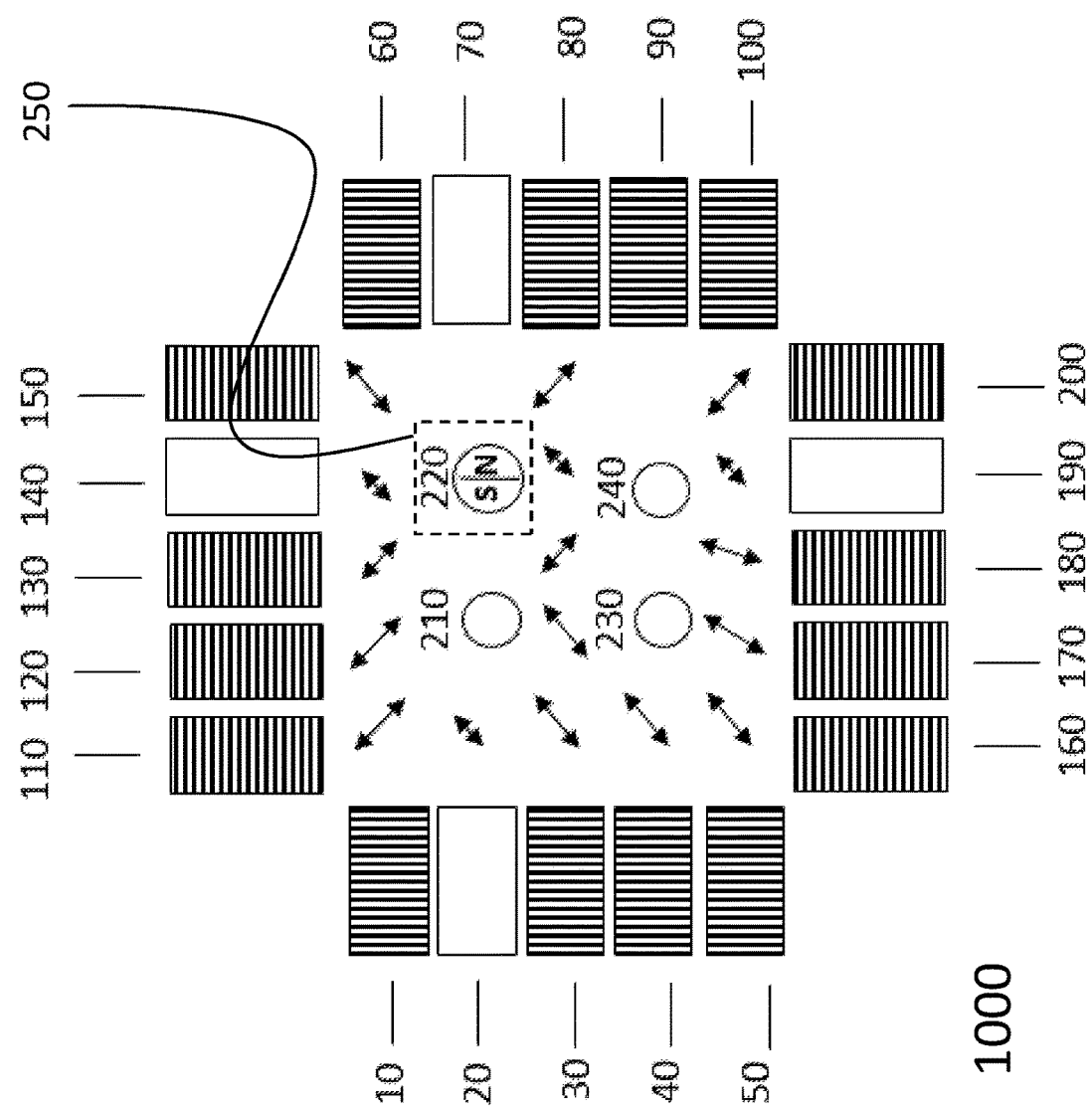
FIG. 2 illustrates an example of the apparatus in a Selective Demagnetization State in accordance with the disclosed embodiments wherein the magnetic configuration of electropermanent magnets and of particles is changed through application of rapidly alternating currents in a subset of the electropermanent magnets.

FIG. 2 illustrates an example of the apparatus 1000 wherein the magnetic configuration of electropermanent magnets is changed through application of rapidly alternating currents in a subset of the electropermanent magnets. For clarity, since the positions of the electropermanent magnets have not changed, they have not been renumbered in FIG. 2. Electropermanent magnets 10 and 30-50, 60, 80-100, 110-130, 150, 160-180 (marked with diagonal lines) have received alternating currents. As a result, the magnetic fields applied by the electropermanent magnets to the region of interest containing the particles (again numbered by locations 210-240) have also rapidly changed in direction.

As shown in FIG. 2, some of the electropermanent magnets 20, 70, 40, 90 have not received alternating currents. As a result of the pattern illustrated in FIG. 2, only one section 250 of the region of interest between the electropermanent magnets is not exposed to the alternating magnetic fields of similar magnitude that the other regions are exposed to. Thus, the particle 220 in this section 250 has not demagnetized. Accordingly, it is shown retaining its prior magnetization with a "S-N" label. The other particles at locations 210, 230, 240 are exposed to alternating magnetic fields represented as double-arrow lines. As a result, particles at locations 210, 230, 240 are demagnetized (as indicated by the absence of an internal label).

For the purposes of this specification, the demagnetization of particles at locations 210, 230, and 240 need not be total to be considered as demagnetization. That is to say the magnetic moment of the particle(s) need not be zero. The demagnetization may be partial. The term demagnetization is thus defined by the ability of the particles to be selectively affected by magnetic fields in subsequent steps of this specification. For example, if the activated electropermanent magnets shown in FIG. 3 apply 0.1 Tesla to the particle at location 210, and the particle moves towards those electropermanent magnets, we may say that the particle was demagnetized in the step shown in FIG. 2. For the purposes of this specification the term "depolarization" and "demagnetization" may be used interchangeably.

For the purpose of clarity in this specification, the configuration of electropermanent magnets and particles shown in FIG. 2 is termed the "Selective Demagnetizing State."

In FIG. 2, the selective region of demagnetization 250 is shown as having a square shape, but it should be understood that the region may have different shapes, depending on the currents that activate the electropermanent magnets and the geometry of the electropermanent magnets. In addition, it should be understood that different subsets of electropermanent magnets (up to and including all electropermanent magnets) may be supplied with alternating currents, with potentially different current strengths, in order to selectively demagnetize different regions in space.

Further, it should be understood that, although the process of creating a selective region 250 with low demagnetization shown in FIG. 2 with electropermanent magnets, such a selective region could also be implemented with different apparatuses that do not use electropermanent magnets, including conventional magnetic gradient systems (which employ large coils) as used in the field of magnetic particle imaging, where a region of zero magnetic field can be created at one location, and that this understanding is part of the specification.

In at least this disclosed embodiment, a major advantage of an electropermanent array (or of similar arrays of small coils) is that it is possible to have multiple regions of low alternating magnetic fields, which can result in low demagnetization of particles in those regions. This property provides the practitioner with more flexibility in designing treatment regimens for location of treatment or surgery in a living body of a particular patient. Similarly, and more generally, this property also provides technical utility for various applications of the disclosed embodiments for any user wishing to move some magnetizable particles in one direction and other magnetizable particles in other directions (for example in a set of microscopic or nanoscopic assembly lines).

Figure 3:
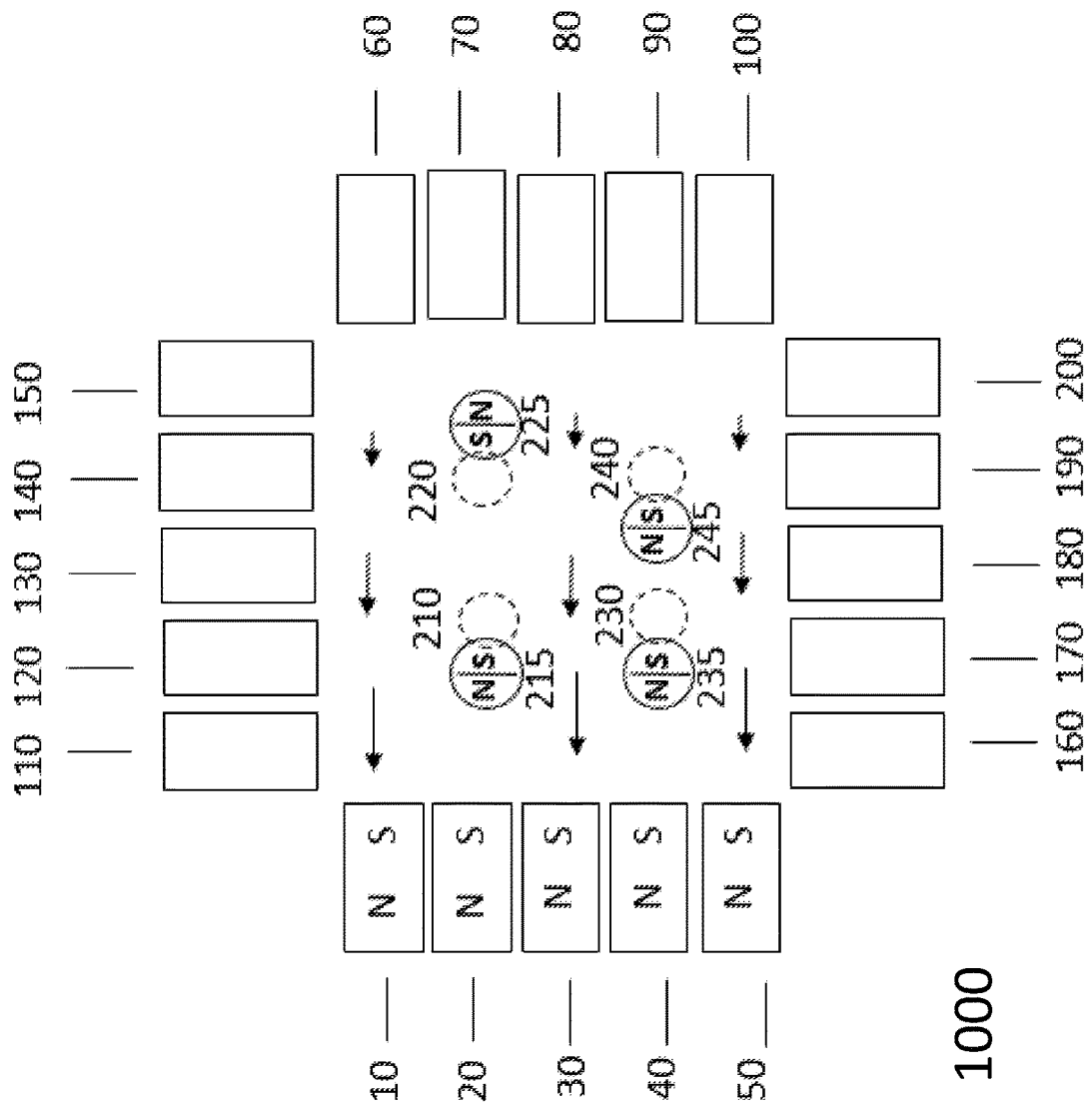
FIG. 3 illustrates an example of the apparatus in a next magnetic configuration of the electropermanent magnet array in a Gradient State in accordance with the disclosed embodiments.

FIG. 3 illustrates an example of the apparatus 1000 in a next magnetic configuration of the electropermanent magnet array in a Gradient State. Immediately prior to implementation of the orientations illustrated in FIG. 3, the electropermanent magnets 10-50 are re-magnetized by passing a current through them. The other electropermanent magnets 60-200 have not been re-magnetized.

For the purposes of this specification, the term "short time" is meant to mean that the time duration is not long enough for the magnetized particles to rotate under the influence of the new magnetic configuration. As a result of the new magnetic state of the electropermanent magnets, a magnetic gradient is generated in the region of interest between the electropermanent magnets. The magnetic gradient is illustrated with arrows of different length to indicate that the magnitude of the magnetic gradient is reduced as the distance increases from electropermanent magnets 10-50.

Of particular technical utility, this magnetic gradient acts on different particles in different ways, depending on whether the particles were previously demagnetized in the prior step (FIG. 2). In this way, the magnetic gradient provides differentiated or selective influence on the particles. The magnetic state of each particle is indicated by the internal label (either "N-S" or "S-N").

As discussed in the '959 Patent, particles can be repelled from electropermanent magnets. Thus, the particle previously at position 220 (as in FIG. 2) may be repelled from electropermanent magnets 10-50. In particular, the particle at position 220 may now move to position 225. That particle may retain most or all of its prior magnetization direction. For example, this retention may be due to the short length of the gradient pulse (which may be too short to overcome the prior magnetization direction).

To the contrary, the other particles were demagnetized in the prior Selective Demagnetization State illustrated in FIG. 2. Thus, those particles are now magnetized by the gradient field and move in the direction of the highest gradient. For example, the particle previously at position 210 in FIG. 2 now moves to position 215 in FIG. 3. Likewise, the particle previously at position 230 in FIG. 2 now moves to position 235 in FIG. 3. Similarly, the particle previously at position 240 in FIG. 2 now moves to position 245 in FIG. 3. The positions of the particles as they were in FIG. 2 are denoted by dashed circles 210, 220, 230, 240, for reference. For the purpose of clarity in this specification, the configuration of electropermanent magnets and particles shown in FIG. 3 is termed the "Gradient State."

Figure 4:
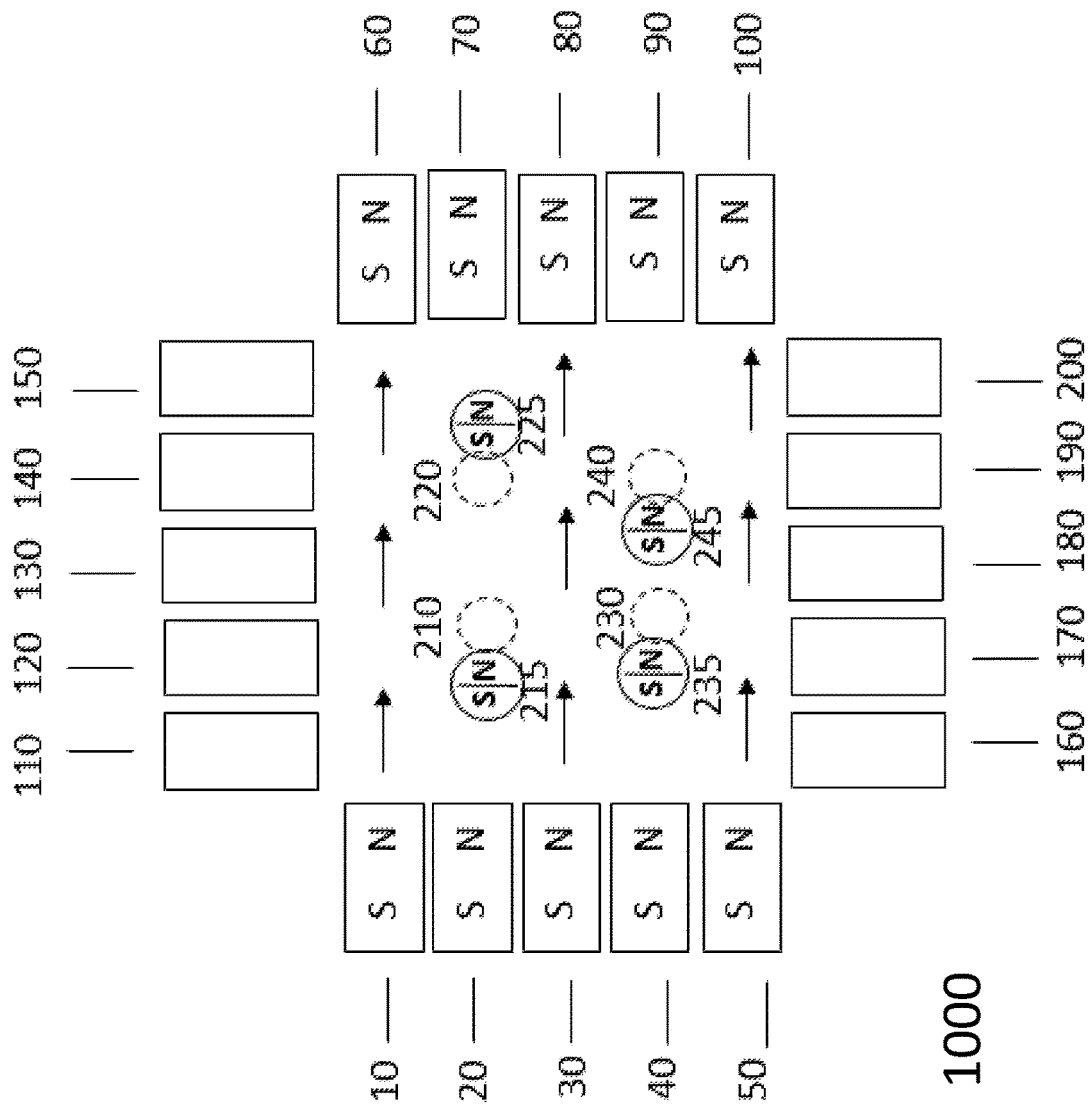
FIG. 4 illustrates an example of the apparatus in a Re-magnetization State wherein electropermanent magnets are re-magnetized to establish a uniform magnetic field in the region of space between the electropermanent magnets in accordance with the disclosed embodiments.

In FIG. 4, electropermanent magnets 10-100 are re-magnetized by passing a pulsed current through them, and a uniform magnetic field is established in the space between the electropermanent magnets. In the presence of a uniform magnetic field, the particles do not move from their positions 215, 225, 235, 245 prior to the current pulse, but their magnetizations change so that the particles are now all polarized in the same direction (as indicated with the internal labels of "N-S" or "S-N"). The prior positions of the particles as they were in FIG. 2 are denoted by dashed circles 210, 220, 230, 240. For the purpose of clarity in this specification, the configuration of electropermanent magnets and particles shown in FIG. 4 is termed the "Re-magnetization State".

Figure 5:
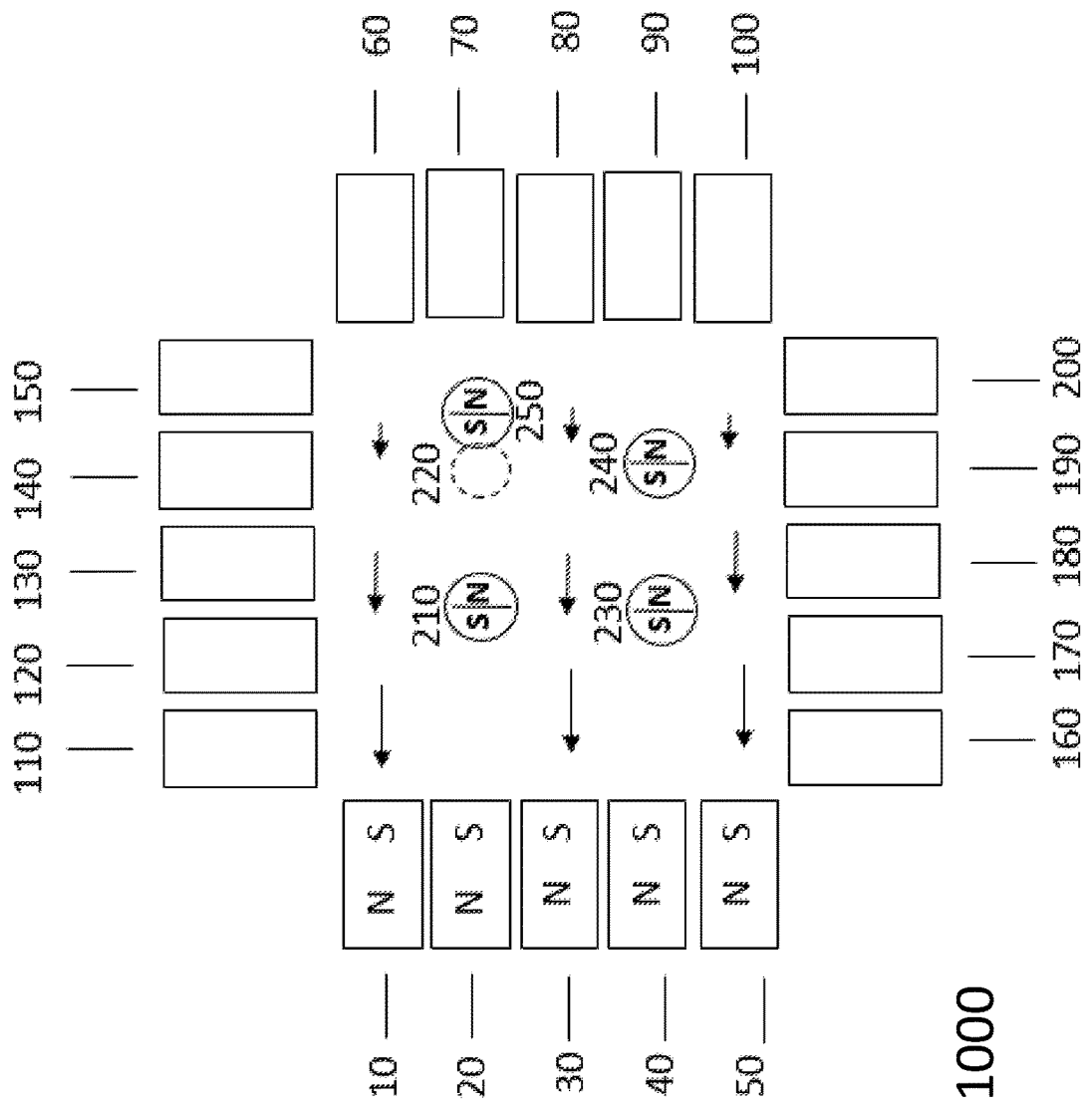
FIG. 5 illustrates the status of the apparatus after application of current pulses through the electropermanent magnets to recreate the electropermanent magnet configuration of FIG. 3 in accordance with the disclosed embodiments.

FIG. 5 shows the status after current pulses have been applied to the electropermanent magnets to recreate the electropermanent magnet configuration of FIG. 3. As shown in FIG. 3, the magnetic gradient transiently repels all particles bringing particles back to their initial positions 210, 230, 240, with the exception of the particle which had been selectively excluded from demagnetization (as illustrated in FIG. 2). That particle, which had initially been at position 220 (shown in a dashed circle) experiences a net translation (over the course of the steps taken from FIGS. 1 to 5) and is, thus, at position 250.

As a result, the operations performed in accordance with the disclosed embodiments provide selective application of magnetizing and demagnetizing pulses to provide selective and/or differentiated positioning of one or more particles in a region of space positioned in-between the electropermanent magnets of the apparatus 1000.

Thus, the disclosed embodiments provide the ability to translate, manipulate, or otherwise actuate at least one particle in one location to another location without translating other particles at other locations. The term "actuate" is meant to include the broad field including methods of converting magnetic fields into other forms of energy. For example, selective motion of particles in one region of space might be used to heat that region. Alternatively, selective torque due to selective motion of particles might create an electric field due to coupling with a piezoelectric material in that region.

Additionally, it should be understood that the above example of creating a selective region of low demagnetization is merely an example of the potential utility of the inventive concepts. Therefore, it should be understood that the disclosed embodiments may be used to create selective regions of different levels of magnetization and/or demagnetization based on the application of different magnetic field levels, and that the use of sequential steps of magnetization and/or demagnetization enables the selective motion and/or activation of magnetic particles.

Further, as explained above, it should be understood that, although the process of creating a selective region with low demagnetization may be performed with electropermanent magnets, such a selective region could also be implemented with different apparatuses that do not use electropermanent magnets, including conventional magnetic gradient systems (which employ large coils) as used in the field of magnetic particle imaging, where a region of zero magnetic field can be created at one location, and that this understanding is part of the specification. Thus, it should be understood that, when electropermanent magnets or other devices capable of generated non-linear magnetic fields are used, it is possible to translate particles in several locations without translating particles in other locations.

Moreover, the application of non-initial, subsequent sequences with different magnetic field configurations enables the positioning of selected particles along selected trajectories and to selected positions over time.

For the purposes of illustration, particles have been represented in the figures as round circles. It should be understood that the term "particles" is broader than only round structures, and that the term "particles" may include, but not be limited to, nano-sized linear particles or to centimeter-sized surgical needles, clamps or other surgical tools, or to parts of another apparatus or tool.

Further, it should be understood that although the figures may represent the particles as having polarization extending throughout the particles, the polarization may be confined to one or more sections of one or more particles. Thus, it should be understood that some of the particles included in a region of interest may have different shapes and/or magnetic properties from other particles in the region of space; this heterogeneity may affect the ability to selectively manipulate one or more of the particles in the region of space.

It should also be understood that, for the purposes of illustration of the technical utility of the disclosed innovation, a specific sequence of magnetic configurations has been presented in the figures. However, the functionality of the disclosed embodiments is not limited to this specific example sequence. Accordingly, it should be understood that the sequence could be altered to obtain a similar desired effect or other effects as should be understood by one of ordinary skill in the art to achieve selective and/or differentiated manipulation of one or more of a plurality of particles included in a region of interest.

Likewise, the present disclosure has described selective translation of particles in a region of interest. Nevertheless, the disclosed embodiments have additional technical utility in that the selective manipulation of particles may include other forms of manipulation of particles, for example, selective vibration of particles, selective heating of particles, selective generation of electric fields though the use of magneto-electric or tribological particle segments, selective actuation of particles to release drugs included in the particles or a part of such parties. Further, these operations may be accomplished using similar methods, apparatuses and/or components thereof.

It should be understood that electropermanent magnets and other sources of magnetic fields include but are not limited to "magnetoelectric material" or "magneto-electric material" or "magnetoelectric composite" or "magneto-electric composite," which encompass substances or combination of substances, in which changes in magnetic properties change in the presence of or application of an electric field.

Those skilled in the art will recognize, upon consideration of the above teachings, that the above exemplary embodiments may perform the above-specified operations (and those referred in the claims) under the control of at least one controller that may utilize or be based upon use of one or more programmed processors programmed with a suitable computer program. However, the disclosed embodiments could utilize one or more controllers implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments.

Furthermore, it should be understood that control and cooperation of components of an apparatus for applying magnetic fields described herein to manipulate the one or more particles may be provided using software instructions that may be stored in a tangible, non-transitory storage device such as a non-transitory computer readable storage device storing instructions which, when executed on one or more programmed processors, carry out the above-described method operations and resulting functionality. In this case, the term non-transitory is intended to preclude transmitted signals and propagating waves, but not storage devices that are erasable or dependent upon power sources to retain information.

Those skilled in the art will appreciate, upon consideration of the above teachings, that the program operations and processes and associated data used to implement certain of the embodiments described above can be implemented using disc storage as well as other forms of storage devices including, but not limited to non-transitory storage media (where non-transitory is intended only to preclude propagating signals and not signals which are transitory in that they are erased by removal of power or explicit acts of erasure) such as for example Read Only Memory (ROM) devices, Random Access Memory (RAM) devices, network memory devices, optical storage elements, magnetic storage elements, magneto-optical storage elements, flash memory, core memory and/or other equivalent volatile and non-volatile storage technologies without departing from certain embodiments of the present invention. Such alternative storage devices should be considered equivalents.

While certain illustrative embodiments have been described, it is evident that many alternatives, modifications, permutations and variations will become apparent to those skilled in the art in light of the foregoing description. While illustrated embodiments have been outlined above, it is evident that many alternatives, modifications and variations will be apparent to those skilled in the art. Accordingly, the various embodiments of the invention, as set forth above, are intended to be illustrative, not limiting. Various changes may be made without departing from the spirit and scope of the invention.

As a result, it will be apparent for those skilled in the art that the illustrative embodiments described are only examples and that various modifications can be made within the scope of the invention as defined in the appended claims.

The invention claimed is:

1. An apparatus for selectively translating, manipulating, or actuating particles in a region of space, the apparatus comprising:
   a power source;
   a plurality of magnetic field sources coupled to the power source for selective application of power to generate magnetic field; and
   a controller coupled to the power source and the plurality of magnetic field sources to control the power source and the plurality of magnetic field sources to produce and vary magnetic field in the region of space to selectively manipulate the plurality of particles in the region of space,
   wherein at least one part of at least one particle of the plurality of particles retains its magnetic polarization after reduction or removal of the produced magnetic field from the at least one part of the at least one particle,
   whereby the at least one particle of the plurality of particles is selectively manipulated by magnetic field in the region of space based on the retained magnetic polarization.

2. The apparatus of claim 1, wherein the controller controls the power source and the plurality of magnetic field sources to apply a sequence of inhomogeneous magnetic field configurations in the region of space.

3. The apparatus of claim 2, whereby at least one part of at least one particle of the plurality of particles retains its magnetic polarization after one or more sequence operations.

4. The method of claim 3, wherein at least one of the sequences includes selective spatially-dependent demagnetization or depolarization of the at least one particle.

5. The apparatus of claim 1, wherein the magnetic field sources are electropermanent magnets to which the power source selectively applies current to generate magnetic field.

6. The apparatus of claim 1, wherein the region of space is located at least partially within a living body, the power source, the plurality of magnetic field sources and the controller are located external to the living body, and the at least one particle is configured to be used as a surgical or therapeutic tool within the living body.

7. The apparatus of claim 1, wherein the at least one particle includes at least one electromagnetic device for stimulating or sensing material within a living body.

8. A method of selectively translating, manipulating, or actuating a plurality of particles in a region of space, the method comprising:

applying a sequence of inhomogeneous magnetic field configurations in the region of space to a plurality of particles using a power source, a plurality of magnetic field sources coupled to the power source, and a controller coupled to the power source and the plurality of magnetic field sources to control the power source and the plurality of magnetic field sources to produce and vary magnetic field in the region of space to selectively manipulate the plurality of particles in the region of space, wherein at least one part of at least one particle of the plurality of particles retains its magnetic polarization after one or more sequence operations, whereby the at least one particle of the plurality of particles is selectively manipulated by magnetic field in the region of space based on the retained magnetic polarization.

9. The method of claim 8, wherein the magnetic field sources are electropermanent magnets to which the power source selectively applies current to generate magnetic field.

10. The method of claim 8, wherein the region of space is located at least partially within a living body, the power source, the plurality of magnetic field sources and the controller are located external to the living body, and the method further comprises using the at least one particle as a surgical or therapeutic tool within the living body.

11. The method of claim 8, wherein at least one of the sequences includes selective spatially-dependent demagnetization or depolarization of the at least one particle.

12. The method of claim 8, wherein the at least one particle includes at least one electromagnetic device for stimulating or sensing material within a living body.

* * * * *